US009453151B2

(12) United States Patent
Koch et al.

(10) Patent No.: US 9,453,151 B2
(45) Date of Patent: Sep. 27, 2016

(54) PRESSURE SENSITIVE ADHESIVES BASED ON RENEWABLE RESOURCES, UV CURING AND RELATED METHODS

(71) Applicant: Avery Dennison Corporation, Pasadena, CA (US)

(72) Inventors: Carol A. Koch, San Gabriel, CA (US); Srikant Pathak, Diamond Bar, CA (US)

(73) Assignee: Avery Dennison Corporation, Glendale, CA (US)

( * ) Notice: Subject to any disclaimer, the term of this patent is extended or adjusted under 35 U.S.C. 154(b) by 234 days.

(21) Appl. No.: 13/706,299

(22) Filed: Dec. 5, 2012

(65) Prior Publication Data
US 2014/0057101 A1 Feb. 27, 2014

Related U.S. Application Data

(60) Provisional application No. 61/621,681, filed on Apr. 9, 2012.

(51) Int. Cl.
| | |
|---|---|
| C08G 59/00 | (2006.01) |
| C09J 137/00 | (2006.01) |
| A23D 9/00 | (2006.01) |
| A61K 8/92 | (2006.01) |
| C09D 11/101 | (2014.01) |
| C09J 163/00 | (2006.01) |
| C09J 163/06 | (2006.01) |
| C09J 191/00 | (2006.01) |
| C09J 7/02 | (2006.01) |
| A61Q 19/00 | (2006.01) |
| A23D 9/02 | (2006.01) |
| C11C 3/00 | (2006.01) |
| C08G 59/32 | (2006.01) |
| C08G 59/68 | (2006.01) |

(52) U.S. Cl.
CPC ............ *C09J 137/00* (2013.01); *A23D 9/00* (2013.01); *A23D 9/02* (2013.01); *A61K 8/922* (2013.01); *A61Q 19/00* (2013.01); *C08G 59/32* (2013.01); *C08G 59/68* (2013.01); *C09D 11/101* (2013.01); *C09J 7/021* (2013.01); *C09J 163/00* (2013.01); *C09J 163/06* (2013.01); *C09J 191/00* (2013.01); *C11C 3/00* (2013.01); *Y10T 428/287* (2015.01); *Y10T 428/2848* (2015.01)

(58) Field of Classification Search
CPC ........................... C09J 163/10; C09J 191/00
USPC ....................................................... 528/405
See application file for complete search history.

(56) References Cited

U.S. PATENT DOCUMENTS

| | | |
|---|---|---|
| 3,304,344 A | 2/1967 | Szawlowski |
| 3,444,116 A | 5/1969 | Gagnon et al. |
| 4,077,927 A | 3/1978 | McPherson |
| 4,151,055 A | 4/1979 | Stueben et al. |
| 4,404,246 A | 9/1983 | Charbonneau et al. |
| 4,659,771 A | 4/1987 | Craig |
| 4,910,287 A | 3/1990 | McLafferty et al. |
| 4,994,537 A | 2/1991 | Craig et al. |
| 5,218,063 A | 6/1993 | Kimball |
| 5,223,558 A | 6/1993 | Ohba |
| 5,514,728 A | 5/1996 | Lamanna et al. |
| 5,536,778 A | 7/1996 | Kreckel et al. |
| 5,670,562 A | 9/1997 | Schilling |
| 5,869,301 A | 2/1999 | Nghiem et al. |
| 5,872,199 A | 2/1999 | Bloembergen et al. |
| 6,103,834 A | 8/2000 | Espinoza |
| 6,121,398 A | 9/2000 | Wool et al. |
| 6,174,990 B1 | 1/2001 | Noda |
| 6,242,593 B1 | 6/2001 | Bloembergen et al. |
| 6,255,367 B1 | 7/2001 | Bitler et al. |
| 6,319,603 B1 | 11/2001 | Komiya et al. |
| 6,427,599 B1 | 8/2002 | Posson et al. |
| 6,528,088 B1 | 3/2003 | Gilleland et al. |
| 6,593,414 B2 | 7/2003 | Benton et al. |
| 6,613,857 B1 | 9/2003 | Koch et al. |
| 6,646,033 B2 | 11/2003 | Wool et al. |
| 6,713,184 B1 | 3/2004 | Ferencz et al. |
| 6,790,271 B2 | 9/2004 | Thames et al. |
| 7,122,592 B2 | 10/2006 | Wentworth et al. |
| 7,163,720 B1 | 1/2007 | Dhaler et al. |
| 7,196,124 B2 | 3/2007 | Parker et al. |

(Continued)

FOREIGN PATENT DOCUMENTS

| | | |
|---|---|---|
| CN | 1133606 | 10/1996 |
| EP | 437001 A1 * | 7/1991 |

(Continued)

OTHER PUBLICATIONS

Akira Isogai et al., "Sizing performance and hydrolysis resistance of alkyl oleate succinic anhydrides," Peer-Reviewed Sizing, Tappi Journal, Jul. 2004, pp. 8-12.

(Continued)

*Primary Examiner* — Wenwen Cai
(74) *Attorney, Agent, or Firm* — Avery Dennison Corporation

(57) ABSTRACT

One embodiment is a pressure sensitive adhesive label or tape that comprises a facestock, and a pressure sensitive adhesive composition disposed on the facestock and the pressure sensitive adhesive composition includes a product made from reacting an epoxidized naturally occurring oil or fat with a dimer acid. Another embodiment of the invention is a method that comprises reacting an epoxidized naturally occurring oil or fat with a dimer acid to form a PSA precursor; coating the PSA precursor onto a carrier and curing the PSA precursor via UV radiation to form a pressure sensitive adhesive.

12 Claims, 4 Drawing Sheets

(56) References Cited

U.S. PATENT DOCUMENTS

| | | |
|---|---|---|
| 7,524,909 B2 | 4/2009 | Palmese et al. |
| 7,682,477 B2 | 3/2010 | Moeller et al. |
| 7,981,988 B2 | 7/2011 | Hyde |
| 8,796,351 B2 | 8/2014 | Koch |
| 2002/0188056 A1 | 12/2002 | Wool et al. |
| 2007/0276108 A1 | 11/2007 | Hyde |
| 2008/0131639 A1 | 6/2008 | Yamamoto et al. |
| 2009/0104448 A1 | 4/2009 | Thompson et al. |
| 2010/0261806 A1 | 10/2010 | Koch |
| 2011/0135924 A1 | 6/2011 | Takahira et al. |
| 2011/0244160 A1 | 10/2011 | Ishiguro et al. |
| 2011/0281045 A1 | 11/2011 | Goubard et al. |
| 2012/0059087 A1 | 3/2012 | Koch et al. |
| 2012/0156484 A1 | 6/2012 | Vendamme et al. |
| 2012/0232226 A1 | 9/2012 | Takahira et al. |
| 2013/0078464 A1* | 3/2013 | Li et al. .......... 428/355 EP |
| 2014/0154506 A1 | 6/2014 | Williams et al. |
| 2014/0342153 A1 | 11/2014 | Li et al. |
| 2015/0099830 A1 | 4/2015 | Koch et al. |

FOREIGN PATENT DOCUMENTS

| | | |
|---|---|---|
| EP | 0992569 | 4/2000 |
| EP | 1640388 | 3/2006 |
| EP | 2290000 | 3/2011 |
| EP | 2439224 | 4/2012 |
| GB | 1279939 | 6/1972 |
| GB | 1298325 | 11/1972 |
| GB | 1373316 | 11/1974 |
| JP | 58001739 | 1/1983 |
| JP | 2008-202015 | 9/2008 |
| JP | 2008-297363 | 12/2008 |
| RU | 2201948 | 4/2003 |
| WO | 91/04151 | 4/1991 |
| WO | 01/00148 | 1/2001 |
| WO | 01/37991 | 5/2001 |
| WO | 2005/061646 | 7/2005 |
| WO | 2006/068483 | 6/2006 |
| WO | 2007/140102 | 12/2007 |
| WO | 2008/144703 | 11/2008 |
| WO | 2009/071554 | 6/2009 |
| WO | 2011/023255 | 3/2011 |
| WO | 2011/112643 | 9/2011 |
| WO | 2011/156378 | 12/2011 |
| WO | 2012/024301 | 2/2012 |
| WO | 2013/086004 | 6/2013 |
| WO | 2013/086014 | 6/2013 |
| WO | 2014/089323 | 6/2014 |

OTHER PUBLICATIONS

Werner J. Blank et al., "Catalysis of the Epoxy-Carboxyl Reaction," Presented at the International Waterborne, High-Solids and Powder Coatings Symposium, Feb. 21-23, 2001.

Tank Eren et al., "Polymerization of Maleic Anhydride-Modified Plant Oils with Polyols," May 24, 2002, Journal of Applied Polymer Science, vol. 90, pp. 197-202.

Junko Asahara et al., Crosslinked acrylic pressure-sensitive adhesives. I. effect of the crosslinking reaction on the peel strength, Journal of Applied Polymer Science, vol. 87, 1493-1499 (2003).

S. Begila David et al., "Studies on acrylated epoxidized triglyceride resin-co-butyl methacrylate towards the development of biodegradable pressure sensitive adhesives," Journal of Materials Science: Materials in Medicine (2009), 20 (Suppl. 1) S61-S70.

Horst Baumann et al., "Natural Fats and Oils—Renewable Raw Materials for the Chemical Industry," Angew. Chem. Int. Ed. Engl. 27:41-62, 1988.

Ursula Biermann et al., "New Syntheses with Oils and Fats as Renewable Raw Materials for the Chemical Industry," Angew. Chem. Int. Ed. 39:2206-2224, 2000.

Z.S. Liu et al., "Solid freeform fabrication of epoxidized soybean oil/epoxy composite with bis or polyalkyleneamine curing agents," Composites Part A 38:87-93, 2007.

Glen Merfeld et al., "Acid/epozy reaction catalyst screening for low temperature (120° C) powder coatings," Progress in Organic Coatings 52(2):98-109, Feb. 1, 2005.

J.O. Metzger et al., "Lipids as renewable resources: current state of chemical and biotechnological conversion and diversification," Appl. Microbial Biotechnical 71:13-22, 2006 (Published online Apr. 8, 2006).

Randal L. Shogren et al., "Biodegradation behavior of some vegetable oil-based polymers," Journal of Polymers and the Environment 12(3):173-178, 2004.

Michael A.R. Meier et al., "Plant oil renewable resources as green alternatives in polymer science," Chemical Society Reviews 36:1788-1802, 2007 (Published online Jul. 23, 2007).

International Preliminary Report on Patentability issued in corresponding IA No. PCT/US2008/064278 dated Oct. 29, 2009.

International Search Report and Written Opinion issued in corresponding IA No. PCT/US2008/064278 dated Nov. 21, 2008.

International Search Report issued in corresponding IA No. PCT/US2008/064278 dated Jan. 15, 2009.

Written Opinion of the International Searching Authority issued in corresponding IA No. PCT/US2008/064278 dated Jan. 15, 2009.

Written Opinion of the International Preliminary Examining Authority issued in corresponding IA No. PCT/US2008/064278 dated Sep. 10, 2009.

International Preliminary Report on Patentability issued in corresponding IA No. PCT/US2011/047930 dated Feb. 28, 2013.

International Search Report and Written Opinion issued in corresponding IA No. PCT/US2011/047930 dated Nov. 8, 2011.

International Preliminary Report on Patentability issued in corresponding IA No. PCT/US2012/067963 dated Oct. 23, 2014.

International Search Report and Written Opinion issued in corresponding IA No. PCT/US2012/067963 dated Feb. 4 2013.

International Preliminary Report on Patentability issued in corresponding IA No. PCT/US2013/073366 dated Jun. 18, 2015.

International Search Report issued in corresponding IA No. PCT/US2013/073366 dated Mar. 21, 2014.

* cited by examiner

PRESSURE SENSITIVE ADHESIVES BASED ON RENEWABLE RESOURCES, UV CURING AND RELATED METHODS

CROSS-REFERENCE TO RELATED APPLICATION

The present application claims the benefit of U.S. Provisional Application No. 61/621,681 filed Apr. 9, 2012, which is incorporated herein by reference in its entirety.

BACKGROUND

The present invention relates generally to the field of pressure sensitive adhesives (PSAs). More specifically, the invention relates to pressure sensitive adhesives that are formed from renewable resources, for example bio-based materials, and methods for forming the pressure sensitive adhesives.

SUMMARY

In one aspect, the invention provides methods of forming pressure sensitive adhesives. The methods comprise reacting an epoxidized naturally occurring oil or fat with a dimer acid to form a pressure sensitive adhesive precursor. In another embodiment of the invention, the method further comprises radiation curing of the pressure sensitive adhesive precursor. In a further embodiment of the invention, the method comprises UV curing and thermal post cure.

In another embodiment, a method comprises reacting an epoxidized naturally occurring oil or fat with at least one dimer acid and at least one diacid to form a pressure sensitive adhesive precursor.

In another embodiment, a method comprises reacting an epoxidized naturally occurring oil or fat with at least one dimer acid, and at least one additional component selected from one or more of monoepoxides, monoacids, polyols, biobased polyols, UV enhancers, and catalysts to form a pressure sensitive adhesive precursor.

In a further embodiment, a method of forming a pressure sensitive adhesive is provided which comprises reacting an epoxidized naturally occurring oil or fat with a diacid to form a pressure sensitive adhesive precursor; adding a photo catalyst to pressure sensitive adhesive precursor; and curing the pressure sensitive adhesive precursor using UV radiation to form a pressure sensitive adhesive.

In another embodiment, a method comprises reacting an epoxidized naturally occurring oil or fat with a dimer acid to form a PSA precursor; coating the PSA precursor onto a carrier; and curing the PSA precursor to form a pressure sensitive adhesive.

In a further embodiment, a method of forming a pressure sensitive adhesive comprises reacting an epoxidized naturally occurring oil or fat with at least one additional reagent to form a PSA precursor at an elevated temperature for a given time period; mixing a photoacids generator with the PSA precursor at an elevated temperature; applying the PSA precursor onto a carrier; and curing the PSA precursor with radiation to form a pressure sensitive adhesive.

The invention also provides pressure sensitive adhesives formed by these methods.

In another aspect, the present invention provides pressure sensitive labels or tapes which include a facestock, and pressure sensitive adhesive that includes a product made from reacting an epoxidized naturally occurring oil or fat with a dimer acid. In another embodiment of the invention, the facestock comprises materials made from renewable resources.

As will be realized, the invention is capable of other and different embodiments and its several details are capable of modifications in various respects, all without departing from the invention. Accordingly, the description is to be regarded as illustrative and not restrictive.

DETAILED DESCRIPTION

Figure 1:
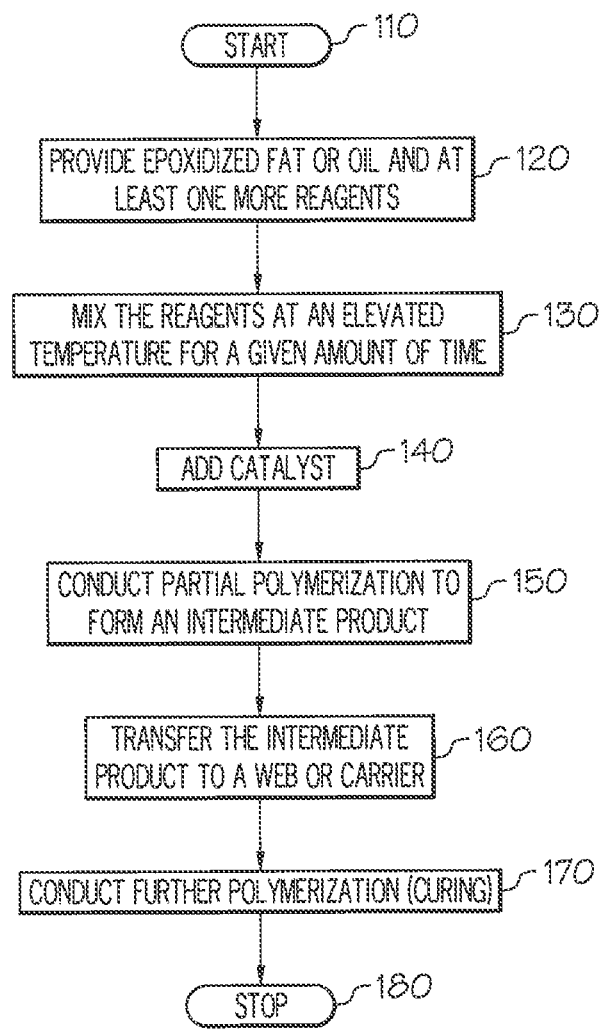
FIG. 1 is a flow chart illustrating one embodiment of the invention.

In various embodiments of the invention, pressure sensitive adhesives are produced from one or more naturally occurring fats and/or oils. The natural fats or oils are epoxidized and reacted with one or more dimer acids, diacids or combinations thereof to produce the inventive pressure sensitive adhesives. In other embodiments of the invention, pressure sensitive adhesives are produced from biologically based or bio-based glycerol esters. As will be appreciated, glycerol esters include monoglycerides, diglycerides, triglycerides, and combinations thereof. The biobased glycerol esters are epoxidized and reacted with one or more dimer acids, diacids, or combinations thereof. The formulation is thermally cured, radiation cured, or combinations thereof to produce the pressure sensitive adhesives. These and other aspects are described herein as follows.

The terms "naturally occurring" or "natural" fats and/or oils as used herein generally refer to fats or oils that are obtained from plants, algae or animals as opposed to such materials obtained from petroleum or other fossil fuels. Thus, the terms "naturally occurring" or "natural" exclude oils or other materials that are obtained either directly or indirectly from petroleum sources or fossil fuel sources. As will be appreciated, examples of fossil fuels include coal, petroleum based oil, and gas. The natural fats and/or oils referred to herein include fats and/or oils that are obtained from plants, algae or animals and also to such fats and/or oils which have been subjected to various purification, processing, or chemical reactions.

The term "bio-based" when used in association with glycerol esters, monoglycerides, diglycerides, triglycerides, and combinations thereof, refers to such agents that are obtained from naturally occurring fats and/or oils.

The term "renewable resource" refers to natural resources with the ability of being replaced through biological or other natural processes and replenished with the passage of time, typically on an annual basis.

Throughout the disclosure, the term "fat", "oil" and other reagents are referred to in singular and plural forms interchangeably, unless otherwise specified. It should be understood that the reference to each reagent also includes other components, mixtures or impurities that exist naturally with such reagent, or as a result of the process to obtain such reagents. For example, the dimer acid used in the invention may be a mixture of monoacids, dimer acids, and trimer acids, and the diacid used in the invention may be a mixture of diacids.

Examples of natural fats and oils from plant, algae or animal sources include, but are not limited to, soybean oil, palm oil, olive oil, corn oil, canola oil, linseed oil, rapeseed oil, castor oil, coconut oil, cottonseed oil, palm kernel oil, rice bran oil, safflower oil, sesame oil, sunflower oil, tall oil, lard, tallow, fish oil, and combinations thereof. Typically, the fatty acids associated with natural fats and oils include long chain, e.g. $C_8$ to $C_{22}$, moieties, many of which include multiple double bonds per chain. The glycerol molecule has three hydroxyl (OH—) groups. Each fatty acid has a carboxyl group (COOH—). In triglycerides, the hydroxyl groups of the glycerol join the carboxyl groups of the fatty acids to form ester bonds.

Oils contain a distribution of the fatty acids depending on the source. Table 1 is a list of the percentage of various fatty acids in some common oils and fats. Though the unsaturation, represented by the number of double bonds, serves as a potential reaction site for polymerization, the double bonds are relatively unreactive unless conjugated as in drying oils such as Tung oil. In one or more embodiments described herein, however, the double bonds are modified and polymerization occurs based on the modification.

esters are epoxidized and then reacted with one or more dimer acids, diacids, or combinations thereof.

Epoxidized oils may include epoxidized triglycerides, epoxidized diglycerides, epoxidized monoglycerides, and partially epoxidized equivalents. Examples of commercially available epoxidized soybean oil and its derivatives include, DEHYSOL available from Cognis/BASF, VIKOFLEX available from Arkema, and DRAPEX available from Galata Chemicals. In addition to epoxidized soybean oil, epoxidized palm oil, epoxidized corn oil, epoxidized linseed oil and others are also available commercially and are contemplated as useful in conjunction to the present invention.

The epoxidized naturally occurring fats or oils may also be formed from natural fats or oils. One or more naturally occurring fats or oils may be subjected to a reaction whereby epoxide functional groups are introduced into the triglycerides diglycerides, and/or mono-glycerides of the fats or oils by epoxidation of the double bonds in the glycerides. The epoxidized materials may then be reacted with additional components.

Reacting Epoxidized Oil(s)

As noted, one or more epoxidized natural fats or oils may be reacted with one or more of the following components to form a pressure sensitive adhesive: (i) dimer acid(s), (ii) diacid(s), and combinations thereof.

In addition to the use of one or more of these multifunctional components, one or more monoepoxides, monoacids, alcohol and combinations thereof may be used. Generally, a

TABLE 1

| fatty acid | # of Carbons | # of double bonds | canola | corn | cotton-seed | linseed | olive | palm | rape-seed | soybean | high oleic |
|---|---|---|---|---|---|---|---|---|---|---|---|
| myristic | 14 | 0 | 0.1 | 0.1 | 0.7 | | | 1 | 0.1 | 0.1 | |
| myristoleic | 14 | 1 | | | | | | | | | |
| palmitic | 16 | 0 | 4.1 | 10.9 | 21.6 | 5.5 | 13.7 | 44.4 | 3 | 11 | 6.4 |
| palmitoleic | 16 | 1 | 0.3 | 0.2 | 0.6 | | 1.2 | 0.2 | 0.2 | 0.1 | 0.1 |
| margaric | 17 | 0 | 0.1 | 0.1 | 0.1 | | | 0.1 | | | |
| margaroleic | 17 | 1 | | | 0.1 | | | | | | |
| stearic | 18 | 0 | 1.8 | 2 | 2.6 | 3.5 | 2.5 | 4.1 | 1 | 4 | 3.1 |
| oleic | 18 | 1 | 60.9 | 25.4 | 18.6 | 19.1 | 71.1 | 39.3 | 13.2 | 23.4 | 82.6 |
| linoleic | 18 | 2 | 21 | 59.6 | 54.5 | 15.3 | 10 | 10 | 13.2 | 53.2 | 2.3 |
| linolenic | 18 | 3 | 8.8 | 1.2 | 0.7 | 56.6 | 0.6 | 0.4 | 9 | 7.8 | 3.7 |
| arachidic | 20 | 0 | 0.7 | 0.4 | 0.3 | | 0.9 | 0.3 | 0.5 | 0.3 | 0.2 |
| gadoleic | 20 | 1 | 1 | | | | | | 9 | | 0.4 |
| eicosadienoic | 20 | 2 | | | | | | | 0.7 | | |
| behenic | 22 | 0 | 0.3 | 0.1 | 0.2 | | | 0.1 | 0.5 | 0.1 | 0.3 |
| erucic | 22 | 1 | 0.7 | | | | | | 49.2 | | 0.1 |
| lignoceric | 24 | 0 | 0.2 | | | | | | 1.2 | | |

In certain embodiments of the invention, one or more particular classes of bio-based glycerol esters may be used in forming the pressure sensitive adhesives. For example, glycerol esters include monoglycerides, diglycerides, triglycerides, and combinations thereof. In some embodiments, the glycerol esters include a majority proportion of triglycerides, however, it will be appreciated that the invention includes the use of monoglycerides, diglycerides, and other components associated with the bio-based glycerol esters. As will be appreciated, the monoglycerides and diglycerides typically contain many of the previously noted fatty acids described herein.

Epoxidized Fats and Oils

In present epoxidized naturally occurring fats or oils may be reacted with one or more of dimer acids, diacids, or combinations thereof. More specifically, the reactions may include bio-based glycerol esters, which include triglycerides of the naturally occurring fats or oils. The glycerol difunctional component is utilized for reacting with the epoxidized natural fats or oils in order to obtain a polymeric product having sufficient molecular weight to function as a suitable pressure sensitive adhesive. For certain applications, however, it is contemplated that one or more monofunctional agents may be used to adjust the network density or other characteristics of the resulting polymeric products.

Without being bound by theory, it is believed that the reaction to make a PSA precursor occurs between the acid groups and the epoxy groups. The PSA precursor may then be coated onto a suitable carrier and followed by on web curing or crosslinking to make the PSA. The curing step may be accomplished by thermal means or by radiation means such as UV. The curing mechanism may be defined by reaction between epoxy-epoxy, epoxy-carboxyl, or epoxy-hydroxyl functionalities. Epoxy containing reactive diluents may be added to control the extent of crosslinking and the flexibility of the finished polymer. Without being bound by theory, it is believed that the Tg of the resulting polymer needs to be lower than the temperature the product is intended to be used at. The crosslink density of the resulting polymer needs to be relatively low in order to obtain the properties of a pressure sensitive adhesive, Dimer Acids Made from Fatty Acids The epoxidized fats or oils may be reacted with a dimer acid to form the pressure sensitive adhesives of interest. Dimer acids are dicarboxylic acids formed by the dimerization of unsaturated fatty acids such as oleic acid and linoleic acid. The dimerization conditions result in a mixture of structures including acylic, monocyclic and polycyclic materials. Commercially available dimer acids typically contain a low level of the monoacid, a majority level of the dimer acid, and an amount of polyfunctional or trimer acids as well. Useful dimer acids may be crude, distilled, and hydrogenated. Examples of commercially available dimer acids include, dimer acids from Arizona under the trade name UNIDYME, from Cognis/BASF under the trade name EMPOL, and from Croda under the trade name PRIPOL.

Diacids

The epoxidized fats or oils may be reacted with a diacid to form the pressure sensitive adhesives of interest. Examples of diacids include, but are not limited to, succinic acid, glutaric acid, adipic acid, pimelic acid, suberic acid, azelaic acid and sebacic acid.

Monoacids

Monoacids are also contemplated as useful in conjunction with the present invention. In one embodiment, monoacids are useful to control the extent of crosslink density. Examples include, but are not limited to, fatty acids such as stearic acid, lauric acid, myristic acid, palmitic acid and mixed fatty acids such as coco fatty acids derived from coconut oil Catalysts Catalysts may be employed to improve the reaction rate. Typical catalysts that may be used include, but are not limited to, amines, imidazoles, phenols, and metal complexes. Examples include dimethyl benzyl amine (DMBA), triethylamine, triethanolamine, 2-ethyl-4-methylimidazole, 2,4,6-tris(dimethylaminomethyl)phenol, and chromium acetylacetonate (CrAA). Examples of commercially available activated chromium(III) complexes include, but are not limited to, AMC2 from Ampac, and HYCAT from Dimension Technology Chemical Systems, Inc. Zinc chelate catalysts are also available from King Industries under the trade name NACURE.

Photo Acid Generator (PAG)

The PSA precursor made of reacting epoxidized oil with dimer acids and/or diacids may be further cured. In some embodiments radiation curing may be desirable. When radiation curing is used, a photo catalyst (photo initiator) may need to be added to the product. Typical photo catalysts include, but are not limited to, photoacids generators (PAGs) and photobases generators. Without being bound by theory, it is believed that photoacids may be useful because they are based on long lived H+ catalysts. Therefore, they may not need an inert gas blanket such as nitrogen. Additionally, photoacids are suitable reagents in ring opening polymerization of epoxides. Examples of commercially available photoacids include, but are not limited, UVI-6976, UVI-6992 from Dow Corning, UV 9390C 01P from GE Silicones, and PC 2506 from Polyset Inc. The amount of photoacids may be from about 0.05 to about 5% based on the weight of the starting materials. In some embodiments, the amount of photoacids may be from about 0.1 to 1.5% based on the weight of the starting materials. In some embodiments, lower amount of PAGs and lower doses of energy may be utilized to achieve the same level of cure when there is a high epoxy content in the epoxidized oil. In other embodiments of the invention, photobases may be used. IRGACURE 907 is one example of commercially available photobases.

Polyols

The epoxy group may be reacted with polyols. Polyols may be derived from petroleum such as polybutadiene diol, or derived from plants, such as castor oil or polyols from epoxidized soybean oil. Biobased polyols are commercially available, including, but not limited to the Agrol and Diamond products from Biobased Technologies, the Renuva product line from Dow, the BiOH products from Cargill, castor oils from Aldrich.

In some embodiments, adding polyols, such as castor oil, to the epoxidized oil and dimer acid and/or diacid formulation, along with photoacids generator, may improve the curing kinetics and performance of the PSA. Without being bound by theory, it is believed that the alcohol may accelerate the ring opening polymerization of the epoxidized oil. The incorporation of alcohol in the PSA formulation may also lead to softer and tackier adhesives. The amount of alcohol relative to the amount of epoxidized fat or oil may be from about 5:95, to about 60:40. Higher amount of PAG may be utilized when the epoxidized fat or oil is lowered to compensate for the drop in cure rate.

Other Additives

As previously noted, in addition to one or more of the previously noted dimer acids, diacids, various epoxidized naturally occurring fatty esters, epoxidized fatty acids, or epoxidized diglycerides may be included in the reaction with the epoxidized fats or oils.

Additional additives such as fillers, tackifiers, plasticizers, bio-based tackifiers or plasticizers may also be added to further modify the properties of the resulting pressure sensitive adhesive.

Additional agents containing functional groups such as sulfonic acids, sulfates, phosphates, and the like may also be used to incorporate such functional groups into the resulting polymeric network.

Materials containing either the epoxy group or the hydroxyl group may also be used to incorporate an additional type of functionality. Materials contemplated as useful include, but are not limited to, hydroxyethylacrylate, hydroxylethylmethacrylate, hydroxypropylacrylate, hydroxypropylmethacrylate, hydroxybutylacrylate, hydroxybutylmethacrylate, glycidylmethacrylate, and combinations thereof.

One or more solvents may also be added to the reagents, the reagent mixture, and/or to the resulting polymeric products. A wide array of solvents may be used such as organic solvents. Exemplary organic solvents include, but are not limited to heptane or toluene.

A range of other additives may be added to further modify the adhesive behavior or to improve the processing such as coating or curing of the described bio-based pressure sensitive adhesive. Such additives may enhance the peel behavior on low surface energy substrates, such as polyethylene (PE), polypropylene (PP) and the likes. Examples of additives contemplated as useful include, but are not limited to, rosin based tackifiers such as Foral 85.

Additives may also be used to further improve the curing speed or significantly lower the amount of catalysts for a given cure rate. For example, multifunctional molecules, such as molecules containing more than one hydroxyl, carboxylate, thiol, vinyl ether, silane, siloxane or epoxy functionalities may serve to amplify the crosslinking effect by providing additional crosslinkable sites. Non-limiting examples of such additives include, methyltriethoxysilane, tetraethyl orthosilicate, 1,4-cyclohexanedimethanol diglycidyl ether, pentaerythritol, tetra(ethylene glycol dimethyl ether) and its derivatives. In general such additives may be used in a concentration of up to about 10% by weight of the starting polymer. Such additives may facilitate the crosslinking by enhancing the generation of photoacids or by providing additional crosslinkable sites.

In addition, additives that can enhance the UV absorption, known as UV enhancer or sensitizers, may be added to further improve the curing kinetics. Examples of such additives include anthracene, acetophenone, benzophenone and the like, and any UV initiators. For example, isopropyl-9H-thioxanthen-9-one (ITX, a UV enhancer) at about 1% to about 5% of the total weight may significantly improve curing kinetics along with PAGs compared to PAGs alone.

Although the use of fossil-based components in the formation of the PSAs is generally not preferred, it will be understood that the present invention includes the use of such components as additives in order to obtain certain desired properties or characteristics in the resulting network. For example, the invention includes combining the pressure sensitive adhesives described herein, with one or more components that are obtained or produced from nonrenewable resources such as fossil fuel derived polymers or components. In this regard, pressure sensitive adhesives formed from natural fats and/or oils as described herein can optionally be combined with polymers obtained from non-renewable resources that contain acrylic or epoxide functionality or other pendant groups to selectively adjust or control the properties of the resulting material. A non-limiting example of such property is crosslink density. Techniques based upon this strategy enable a formulator to specifically tailor and/or adjust the properties and performance characteristics of the end product material. This technique enables particular "balancing" of properties of the resulting material. In one embodiment of the invention, the proportion of material originating from renewable resources is at least 25% and in a further embodiment, at least 75%.

Reaction Methods

In one embodiment of the invention, the reaction between one or more epoxidized natural oils and/or fats, and more specifically between the bio-based epoxidized glycerol esters and triglycerides therein, and one or more (i) dimer acids, (ii) diacids, or their combinations is performed at elevated temperatures and optionally with catalyst(s) to increase the speed of the reaction. It will be appreciated that although the description herein is generally provided in terms of reacting epoxidized triglycerides obtained from bio-based oils and/or fats, the invention also includes the use of monoglycerides, diglycerides and various combinations thereof.

In one embodiment of the invention, the reaction is performed in a reactor and at conditions sufficient to achieve a conversion high enough to obtain a coatable syrup, which is a flowable viscous material. The flowable, relatively viscous material is then deposited on a web or other suitable member at sufficiently high temperatures in the presence of a catalyst to accelerate the conversion.

More specifically, the various inventive pressure sensitive adhesives may be formed using an array of polymerization techniques. For example, the reactions can proceed by several techniques such as, but not limited to, bulk polymerization, solvent polymerization, and web polymerization. It is also contemplated that combinations of these techniques may be employed. It is also contemplated that one or more of these techniques utilize photocatalytic cationic polymerization to achieve the desired polymeric product(s).

In a bulk polymerization method, mass polymerization is performed by increasing temperature and optionally adding one or more soluble initiators to the epoxidized natural fats or oils in a liquid state.

The reaction may be batch reaction, fed batch reaction, or continuous reaction. When epoxidized oil is reacted with dimer acid and diacid, fed batch reaction may allow higher incorporation of diacids. In the fed batch reactions, a fraction of components may be added initially, and the balance may be added at given intervals. This fedbatch reaction can make a PSA precursor with very high viscosity without significant gelation.

For certain applications and/or polymerization techniques, it may be desirable for the multifunctional component(s) to constitute the majority of the starting material. As previously noted, one or more monofunctional agents may be added to control or otherwise adjust the crosslink density. If, however, an excess amount of multifunctional components are used in solvent-based polymerization at high concentrations, gelation may occur, resulting in insoluble materials that are not easily coatable and generally not suitable for pressure sensitive adhesives. Therefore, it may be preferred that the multifunctional components constitute a minority proportion of the starting material. The particular proportions utilized for the multifunctional components and other components used in the reaction systems depends upon an array of factors including, but not limited to, the number of functional groups and the molecular weight of the constituents.

The pressure sensitive adhesives may also be formed using web polymerization techniques. In this approach, the PSA precursor, a relatively viscous reaction mixture, is initially formed and then deposited on a web or other member and the reaction allowed or otherwise promoted to proceed to thereby produce the inventive pressure sensitive adhesive.

In some embodiments, the reagents may be partially polymerized to form a PSA precursor. The PSA precursor may then be transferred to a web, line, or other receiving surface. Once appropriately deposited or otherwise applied to a surface or component of interest, the PSA precursor may be subjected to further polymerization to obtain the inventive pressure sensitive adhesive. FIG. 1 is a flow chart illustrating such a process. The process starts at step 110. At step 120, the epoxidized fat or oil and at least one more reagent are provided. The at least one more reagent may be dimer acid, diacid, or combinations thereof. The reagents are mixed at an elevated temperature for a given amount of time at step 130. Optionally, catalysts are added at step 140. Then, at step 150, the reagents are allowed to partially polymerize at the elevated temperature for a given amount of time. The partial polymerization can be transitioned to the next step when a flowable PSA precursor having a viscosity that is appropriate for applying the material as a coating on a web is formed. The appropriate viscosity may be from a few centipoises (cP) to thousands of poises at the coating condition, depending on the method of application. Another parameter that can be used to indicate the end of this partial polymerization is percent gel. The percent gel is 0 at the beginning of the reaction. When the value reaches to a low level, for example, about 1%, the partially polymerized material may be transferred to the next step. Partial polymerization may be performed by exposing the reaction mixture to an appropriate amount of heat and/or radiation. Next, at step 160, the PSA precursor is transferred to a web or other suitable carrier. One exemplary transfer method is through coating. The suitable carrier can be a release liner, a facestock, paper or polymeric film. At step 170, further polymerization is performed such as by exposure to additional heat and/or radiation. The process stops at step 180. Thus, the invention includes combinations of operations such as an initial polymerization of components with bulk polymerization to obtain a desired viscosity of the system, followed by application of the intermediate, partially polymerized product onto a surface of interest, followed by further polymerization of the product with web polymerization while on the surface of interest.

Figure 2:
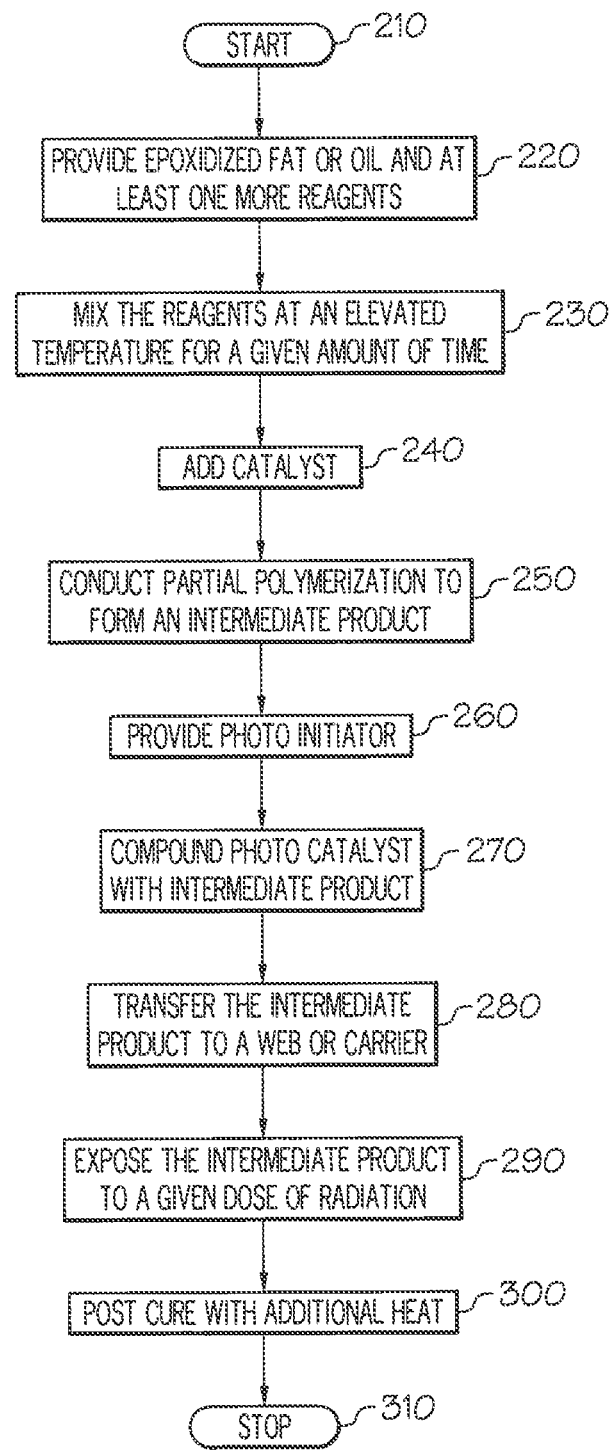
FIG. 2 is a flow chart illustrating one embodiment of the invention.

In one embodiment of the invention, thermal polymerization is used for the initial in-reactor phase of polymerization to make the PSA precursors. Radiation curing followed by heat treatment may then be used for the on web polymerization and curing. FIG. 2 is a flow chart further illustrating such process. The process starts at step 210. At step 220, the epoxidized fat or oil and at least one more reagents are provided. The at least one more reagents may be dimer acid, diacid, or combinations thereof. The reagents are mixed at an elevated temperature for a given amount of time at step 230. Optionally, catalysts are added at step 240. Then, at step 250, the reagents are allowed to partially polymerize at the elevated temperature for a given amount of time to form a PSA precursor. A photo initiator may be provided at step 260, followed by compounding the photo initiator with the PSA precursor at step 270. The photo initiators can be photoacids, photobases, or other suitable species. Next, at step 280, the PSA precursor may be transferred to a web or other suitable carrier. At step 290, further polymerization is performed by exposure to radiation source at a given dose. UV is an exemplary, but non-limiting, radiation source for such purpose. At step 300, the sample is post cured by exposure to additional heat at a given time. The process stops at step 310.

The pressure sensitive adhesives according to the invention may be used as removable or permanent adhesives on paper or film facestocks in a variety of applications ranging from general purpose labels, office product labels, industrial tapes, and medical applications. The facestock may be paper, coated paper, foam, polymer film, clear, opaque, translucent or metalized plastic film, metalized paper, paper backed foil, metal foil, woven, non-woven, fabric, reinforced materials and recycled paper. The facestock may be formed from bio-based polymers. The substrate to be labeled may be a bottle, a can, a container, a vessel, a bag, a pouch, an envelope, a parcel, a box and a cardboard box. The bio-based PSA may cover the full face of the facestock, or pattern coated. The bio-based PSA may be used in combination with PSA derived from petroleum based resources to achieve desired properties or cost savings. Non-limiting exemplary configurations include multilayer PSA with bio-based PSA as one of the layers, or pattern coated PSA with bio-based PSA as one of the pattern forming PSAs.

Radiation Curing of the Bio-Based PSA Formulations

The bio-based PSA formulation of the current invention may be cured through thermal heating, radiation curing, or combinations thereof. In some embodiments, radiation curing may provide faster curing speed and therefore, faster production speed. Radiation curing methods include but are not limited to, ultraviolet (UV) curing and electron beam (EB) curing according to the energy source used.

PAGs may be added for UV curing reactions. In choosing photoacids, the solubility of the PAG in the epoxidized oil should be taken into consideration. The solubility of PAGs in epoxidized oil may be improved through extended mixing, or mixing at a higher temperature.

Commercially available photobases may also be used to cure the formulation. IRGACURE 907 is a nonlimiting an example of such photobases. It can cure DRAPEX 6.8, but requires higher UV doses compared with photoacids at 1 wt % level.

The curing reaction may be conducted using any available UV systems. Examples of such systems include Intelliray 400 desktop UV systems equipped with a 400 W/in (Watts per inch, or WPI) metal halide arc lamp. The dosage of radiation needed to cure the PSA formulation may be related to the type of epoxidized oil, degree of polymerization (in a given system) and may depend on the epoxy content of the molecules. High epoxy content may be cured at relatively low energy doses and at lower PAG concentration.

The degree of cure may be indicated through a number of physical properties, such as viscosity and percent gel. The viscosity rises as the formulation thickens and cures. The percent gel is a measure of the amount of materials that has been crosslinked, and may be represented by a percentage of insoluble portions in the total amount of materials for a given solvent.

The formulation may be further post-cured through thermal heating. Without bound by theory, it is believed that the thermal heating increases the reaction primarily by increasing the diffusion rate. A thermal post-cure may reduce the amounts of PAG necessary to achieve the same gel content. The thermal cure may be delivered by means known to persons skilled in the art, such as through heat tunnel, oven, infrared lamps, and/or hot rollers.

Modification of Epoxidized Fats or Oils

In some embodiments, the adhesive may be cured by incorporating reagents with vinyl, acrylic or methacrylic functional groups during the polymerization of epoxidized fats or oils and the dimer acid or diacid. The acrylic functional groups may be incorporated onto the polymer by reacting acid containing acrylic monomers such as acrylic acid or methacrylic acid, or by reacting hydroxyl containing acrylic monomers such as hydroyxethylacrylate or hydroxyethylmethacrylate, or by reacting epoxy containing acrylic monomers such as glycidylmethacrylate. Once the acrylic functionality is available on the epoxidized fats or oils and dimer acid/diacid polymer, it may be formulated with multifunctional acrylates such as hexanedioldiacrylate and UV photoinitiators such as benzophenone, and coated on release or facestock and then cured via UV radiation.

Test Methods

180 Degree Peel

Samples of the adhesive either directly coated on PET film or laminated to PET film from the release liner were cut into about 2.54 cm by about 20 cm test strips. They were rolled down on a test panel of stainless steel, HDPE or cardboard with a 2 kg rubber clad steel roller moving back and forth at a rate of about 30 cm/min. After a dwell time of 24 hours, the test strips were peeled away from the test panel in an Instron Tensile Tester at 180 degree to the test panel, i.e., folded back on itself and parallel to the surface of the panel, at a rate of about 30 cm/min. The force to remove the adhesive strip from the test panel was measured in pounds per inch (lb/in). Tests were performed in triplicate and the average value was reported.

Shear

Samples of the adhesive coated on PET were laminated to a stainless steel (SS) panel using a 2 kg rubber clad steel roller with a free end of the tape extending beyond the plate. The adhesive contact area was 1.27 cm by 1.27 cm. After 20 minutes dwell at room temperature, the plate was placed at a 2° angle from the vertical and a 500 g weight was suspended from the free end. The time to failure in minutes was measured.

Gel

Gel content was measured according to the following method: about 15 mg of the sample was weighed onto a pre-weighed 10 micron polypropylene filter from Millipore Corporation, Bedford, Mass. The weight of the filter (W1) and the weight of the sample (W2) were recorded. The filter was folded into a half-moon shape and heat sealed around the periphery to make a sample pouch, which was then placed in a 22 mL scintillation vial filled with ethyl acetate. The vial was tumbled for 24 hours. The sample pouch was removed from the vial, rinsed with the same solvent, clam shelled in a metal pan, and placed in a 90° C. oven for 3 hours. The sample was weighed again after the drying and its weight (W3) was recorded. The test was repeated three times and the average value is reported here. Gel content, expressed in wt %, was calculated based on the following formula:

$$\text{Gel content} = ((W3-W1)/W2) \times 100$$

Tg

The glass transition temperature (Tg) of each sample was measured using TA Instrument DSC Q2000 at 5° C./min heating rate.

Spherical Probe Adhesion Test (SPAT)

A SPAT tester with 1" diameter stainless steel spherical probe was used to perform analysis with test speed at 0.04 mm/sec, compressive force at 4.5 N.

UV Measurement

Throughout the examples, all UV measurements were performed by UV measuring puck UVIcure Plus supplied by EIT Inc. of Virginia. Unless indicated otherwise only UV-A measurements were provided.

REPRESENTATIVE EXAMPLES

The following are representative examples providing guidance in forming the inventive pressure sensitive adhesives.

Example 1

Epoxidized soybean oil (ESO) (Edenol D81, 6.51 g) and dimer acid (UNIDYME 14, 6.51 g) were mixed in a 50 mL round bottom flask using a magnetic stir bar and heated to 140° C. in a heating mantle. Chromium acetylacetonate (0.016 g) was added and the mixture was polymerized for 20 minutes. The polymer was coated on a 1 mil PET film and cured in the oven at 160° C. for 20 min. The resulting pressure-sensitive adhesive construction results in a peel to stainless steel of 1.27 lbs/in, peel to polyethylene of 0.36 lbs/in and a shear of over 10,000 minutes. The polymer had 84% gel in ethyl acetate and the glass transition temperature by DSC was -18° C.

Example 2

Epoxidized soybean oil (DRAPEX 6.8, 6.51 g), dimer acid (UNIDYME 14, 6.55 g), and adipic acid (0.52 g) were mixed in a 50 mL round bottom flask using a magnetic stir bar and heated to 140° C. in a heating mantle. Chromium acetylacetonate (0.016 g) was added and the mixture was polymerized for 15 minutes. The polymer was coated on a 1 mil PET film and cured in the oven at 160° C. for 20 min. The resulting pressure-sensitive adhesive construction results in a peel to stainless steel of 2.0 lbs/in, peel to polyethylene of 1.0 lbs/in and a shear of over 10,000 minutes. The polymer had 63% gel in ethyl acetate and the glass transition temperature by DSC was -28° C.

Example 3

Epoxidized soybean oil (VIKOFLEX 7170, 5.51 g), dimer acid (UNIDYME 14, 6.50 g), and epoxidized methyl soyate (VIKOFLEX7010, 1.0 g) were mixed in a 50 mL round bottom flask using a magnetic stir bar and heated to 140° C. in a heating mantle. Chromium acetylacetonate (0.017 g) was added and the mixture was polymerized for 25 minutes. The polymer was coated on a 1 mil PET film and cured in the oven at 160° C. for 60 min. The resulting pressure-sensitive adhesive construction resulted in a peel to stainless steel of 1.86 lbs/in, peel to polyethylene of 0.58 lbs/in and a shear of over 1500 minutes. The polymer had 53% gel in ethyl acetate.

Example 4

Partially epoxidized soybean oil (5% oxirane content, 6.50 g), dimer acid (UNIDYME 14, 6.50 g), and adipic acid (0.51 g) were mixed in a 50 mL round bottom flask using a magnetic stir bar and heated to 140° C. in a heating mantle. Chromium acetylacetonate (0.018 g) was added and the mixture was polymerized for 40 minutes. The polymer was coated on a 1 mil PET film and cured in the oven at 160° C. for 60 min. The resulting pressure-sensitive adhesive construction results in a peel to stainless steel of 0.9 lbs/in and a shear of over 10,000 minutes. The polymer gave 11% gel in ethyl acetate.

Example 5

Epoxidized soybean oil (DRAPEX 6.8, 6.5 g), dimer acid (UNIDYME 14, 6.50 g), and adipic acid (0.5 g) were mixed in a 50 mL round bottom flask using a magnetic stir bar and heated to 140° C. in a heating mantle. The mixture was polymerized for 100 minutes then allowed to cool to 90° C. A photo initiator (Polyset PC2506, 0.14 g) was added and the polymer was coated on a 1 mil PET film and cured under medium pressure mercury UV lamps (300 W/in, 150 ft/min line speed, 78 mJ/cm$^2$, 1.2 W/cm$^2$). The resulting pressure-sensitive adhesive construction resulted in a peel to stainless steel of 1.1 lbs/in and a shear of over 2000 minutes. The polymer had 20% gel in ethyl acetate.

Examples 6-10

Examples 6-10 were prepared according to the procedure set forth in example 1. The amount of each component used and the performance of the PSA are summarized in Table 2. As can be observed, most of the examples have peel value on stainless steel greater than 1 lbs/in. Some of the examples have shear value of greater than 10,000 min. The gel percent for those examples range from 20% to 84%.

TABLE 2

| Example No. | ESO source | ESO amount g | Dimeracid source | Dimeracid amount g | Diacid type | Diacid amount g | Temperature C. | THERMAL CURED EXAMPLES Catalyst/photo catalyst* |
|---|---|---|---|---|---|---|---|---|
| 1 | EDENOL D81 | 6.51 | UNIDYME 14 | 6.51 | — | — | 140 | CrAA |
| 2 | DRAPEX6.8 | 6.51 | UNIDYME 14 | 6.55 | ADIPIC ACID | 0.52 | 140 | CrAA |
| 3 | VIKOFLEX 7170 | 6.51 | UNIDYME 14 | 6.50 | — | — | 140 | CrAA |
| 4 | 5% PESO | 6.5 | UNIDYME 14 | 6.50 | ADIPIC ACID | 0.51 | 140 | CrAA |
| 5 | DRAPEX6.8 | 6.5 | UNIDYME 14 | 6.50 | ADIPIC ACID | 0.5 | 140 | POLYSET PC2506° |
| 6 | EDENOL d81 | 6.0 | UNIDYME 14 | 6.0 | — | — | 140 | DMBA |
| 7 | DEHYSOL D81 | 6.52 | UNIDYME 14 | 6.52 | ADIPIC ACID | 0.51 | 100 | CrAA |
| 8 | DEHYSOL D81 | 6.56 | EMPOL1062 | 6.50 | ADIPIC ACID | 0.50 | 140 | CrAA |
| 9 | DEHYSOL D81 | 6.5 | UNIDYME 14 | 6.51 | — | — | 140 | AMC2 |
| 10 | DRAPEX6.8 | 6.51 | EMPOL1062 | 6.50 | ADIPIC ACID | 0.50 | 140 | AMC2 |

| Example No. | Catalyst amount g | Time polymerization min | Curing temperature C. | Curing time min | Peel-55 LBS/IN | Peel-HDPE LBS/IN | Shear min | gel % | Tg C. |
|---|---|---|---|---|---|---|---|---|---|
| 1 | 0.016 | 20 | 160 | 20 | 1.27 | 0.36 | >10000 | 84 | −18 |
| 2 | 0.016 | 15 | 160 | 20 | 7.0 | 1.0 | >10000 | 63 | −28 |
| 3 | 0.017 | 25 | 160 | 60 | 1.86 | 0.58 | 1500 | 53 | — |
| 4 | 0.018 | 40 | 160 | 60 | 0.9 | — | >10000 | 11 | — |
| 5 | 0.14 | 300 W/IN | — | — | 1.1 | — | 2000 | 20 | — |
| 6 | 3 DROP | 25 | 160 | 160 | 0.23 | — | >10000 | 54 | — |
| 7 | 0.018 | 130 | 160 | 40 | 1.5 | 1.1 | >10000 | 62 | — |
| 8 | 0.017 | 120 | 160 | 20 | 1.27 | 0.51 | >10000 | 59 | — |
| 9 | 4DROP | 10 | 160 | 20 | 1.53 | — | 500 | 77 | — |
| 10 | 4DROP | 5 | 160 | 20 | 2.76 | 1.5 | 95 | 66 | — |

Examples 11 to 15

For example 11 to 15, Intelliray 400 desktop UV system with a flux of about 90 mW/cm$^2$ (UV-A) was used as the source of UV. An infrared lamp of 250 WPI placed about 10 inches from the sample was used for the thermal post cure.

Epoxidized soybean oil (DRAPEX 6.8, 6.5 g), and adipic acid (2.0 g) were mixed in a 50 mL round bottom flask using a magnetic stir bar and heated to 140° C. in a heating mantle. The mixture was polymerized for 20 minutes then a photo initiator (UVI-6976) was added. The mixture was mixed for about 15 minutes. The polymer was coated on a 1 mil PET film and cured under intelliray −400 UV lamps with about 90 mW/cm$^2$, for various amount of time, followed by 1 min of IR lamp exposure. Table 3 is a summary of the percent gel measured in ethyl acetate. Each resulting polymer was tacky to the touch. With one drop of PAG (example 14), a two second UV cure at 90 mW/cm$^2$ dose created comparable gel percent to a 20 minute thermal cure at 160° C. With overnight aging, the percent gel reached the upper 70 percentile. The results show that UV curing does lead to very high gel % in these polymers. Additionally, a small amount of UVI-6976 was necessary to crosslink these polymers and produce an initially very tacky film.

TABLE 3

| | | | % gel | | | | | |
|---|---|---|---|---|---|---|---|---|
| | | | | 2 s @ 90 mW/cm2 | | 5 s @ 90 mW/cm2 | | 10 s @ 90 mW/cm2 | | Thermal Cure |
| Example | PAG Concentration | Out of Reactor | Initial | 24 hour aging | Initial | 24 hour aging | Initial | 24 hour aging | (160 C. for 20 mins) |
| 11 | 7 drops (~0.14 g) | 43a | 72 | | 74 | | 72 | | 75 |
| 12 | 5 drops (~0.10 g) | 3 | 77 | | 78 | | 77 | | 52 |
| 13 | 3 drops (~0.06 g) | 1 | 71 | 78 | 77 | 78 | 75 | 79 | 56 |
| 14 | 1 drop (~0.03 g) | 1 | 63 | 76b | 69 | 75b | 70 | 75b | 62 |
| 15 | no PAG | 2 | | | | | | | | anext day setup
bweekend tumbling in ethyl acetate

Examples 16 to 18

In Example 16 to 18, various amounts of monofunctional epoxy, 1,2 epoxydodecane were added to DRAPEX 6.8, Table 4 is a summary of the observations on the UV curing behavior of each example. The glass transition temperature of example 16 was −19° C. and that of example 18 was lowered to −33° C. The results demonstrated that using monofunctional epoxy can be effective to lower the Tg of the resulting polymer.

TABLE 4

| Example | Drapex 6.8 (g) | 1,2 Epoxydodecane (g) | UV-6976 (mg) | Tg (degree C.) |
|---|---|---|---|---|
| 16 | 0.5 | 0.1 | ~5 mg, 1 wt % of Drapex 6.8 | −19 |
| 17 |  | 0.2 |  |  |
| 18 |  | 0.3 |  | −33 |

Examples 19-32

Examples 19 to 32 were prepared according to the procedure set forth in example 5 with the photo initiator Polyset PC2506 being replaced with various types of PAGs at various amounts. For each example, the sample was exposed to a different dose of the UV radiation through varying the number of passes the sample took under the UV source. Most of the samples were cured using Lesko Conveyer UV systems fitted with a magnetron driven Uvitron D-bulb with a dose of 225 mJ/cm$^2$ (1.3 W/cm$^2$) at 50 ft/min in the center of conveyer. Example 31 and 32 were cured with America Ultraviolet using a dose of 230 ml/cm$^2$ (about 900 mW/cm$^2$ of flux or irradiance) at 50 ft/min measured at the center of the conveyer. Table 5 is a summary of the properties. The results indicate that the percent gel increases with increased UV doses. Most of the samples have acceptable peel to stainless steel. Example 20 and 21 achieved shear value over 10,000 min.

TABLE 5

| Example # | Components | Heat Cure Conditions | UV cure Dose | % Gel | Peel (SS) AVG | lbs/in STD | Failure Mode (FM) | Shear (min) |
|---|---|---|---|---|---|---|---|---|
| 19 | 6.5 g Drapex 6.8 | 110 min | Out of Reactor | 0.5 | AVG | STD | FM |  |
|  | 6.5 g New Unidyme 14 | 140-149 C. | 3 passes (50 ft/min) | 33 | 1 | 0.05 | cohesive | 4.3 |
|  | 0.5 g Adipic Acid |  | 5 passes (50 ft/min) | 40 | 0.9 | 0.2 | stain | 215.5 |
|  | 15 drops UVI 6976 |  | 7 passes (50 ft/min) | 55 | 0.8 | 0.05 | stain | 335.6 |
|  |  |  | 60 min @ 160 C | 25 |  |  |  |  |
| 20 | 6.5 g Drapex 6.8 | 110 min | Out of Reactor | 0.6 | Avg | STD | FM |  |
|  | 6.5 g New Unidyme 14 | 140-146 C. | 3 passes (50 ft/min) | 44 | 0.48 | 0.03 | clean | 1879.7 |
|  | 0.5 g Adipic Acid |  | 5 passes (50 ft/min) | 46 | 0.68 | 0.09 | clean | 10K |
|  | 20 drops UVI 6976 |  | 7 passes (50 ft/min) | 46 | 0.73 | 0.03 | clean | 10K |
|  |  |  | 60 min @ 160 C | 37 |  |  |  |  |
| 21 | 6.5 g Drapex 6.8 | 105 min | Out of Reactor | 0.3 | Avg | STD | FM |  |
|  | 6.5 g New Unidyme 4 | 140-156 C. | 3 Pass (50 ft/min) | 44 | 1.29 | 0.03 | 50 CF | 10K |
|  | 0.5 g Adipic Acid |  | 5 Pass (50 ft/min) | 46 | 1.33 | 0.02 | 50% CF | 10K |
|  | 15 drops UVI 6976 |  | 7 Pass (50 ft/min) | 48 | 1.3 | 0.01 | cohesive | 10K |
| 22 | 6.5 g Drapex 6.8 | 90 min | Out of Reactor | 1 | Avg | STD | FM |  |
|  | 6.5 g New Unidyme 14 | 140-145 C. | 3 Pass (50 ft/min) | 37 | 1.59 | 0.03 | cohesive |  |
|  | 0.5 g Adipic Acid |  | 5 Pass (50 ft/min) | 39 | 1.5 | 0.06 | cohesive |  |
|  | 15 drops UVI 6976 |  | 7 Pass (50 ft/min) | 44 | 1.29 | 0.09 | cohesive |  |
| 23 | 6.5 g Drapex 6.8 | 105 min | Out of Reactor | 0.6 | Avg | STD | FM |  |
|  | 6.5 g New Unidyme 14 | 140-146 C. | 3 Pass (50 ft/min) | 44 | 1.24 | 0.07 | 50% CF |  |
|  | 0.5 g Adipic Acid |  | 5 Pass (50 ft/min) | 45 | 1.5 | 0.02 | 50% CF |  |
|  | 17 drops UVI 6976 |  | 7 Pass (50 ft/min) | 47 | 1.34 | 0.03 | 50% CF |  |
| 24 | 6.5 g Drapex 6.8 | 100 min | Out of Reactor | 0.6 | Avg | STD | FM |  |
|  | 6.5 g New Unidyme 14 | 140-149 C. | 3 Pass (50 ft/min) | 44 | 1.62 | 0.06 | cohesive |  |
|  | 0.5 g Adipic Acid |  | 5 Pass (50 ft/min) | 45 | 1.51 | 0.02 | cohesive |  |
|  | 20 drops UVI 6976 |  | 7 Pass (50 ft/min) | 47 | 1.43 | 0.06 | cohesive |  |
| 25 | 6.5 g Drapex 6.8 | 85 min | Out of Reactor | 0.3 | Avg | STD | FM |  |
|  | 6.5 g New Unidyme 14 | 140-148 C. | 3 Pass (50 ft/min) | 35 | 1.48 | 0.04 | mix |  |
|  | 0.5 g Adipic Acid |  | 5 Pass (50 ft/min) | 40 | 1.55 | 0.02 | mix | 43.2 |
|  | ~100 mg UV 9390C |  | 7 Pass (50 ft/min) | 41 | 1.23 | 0.05 | 25% Tr | 64.1 |
| 26 | 6.5 g Drapex 6.8 | 90 min | Out of Reactor | 0.5 | Avg | STD | FM |  |
|  | 6.5 g New Unidyme 14 | 140-148 C. | 3 Pass (50 ft/min) | 51 | 0.56 | 0.06 | clean | 10K |
|  | 0.5 g Adipic Acid |  | 5 Pass (50 ft/min) | 53 | 0.61 | 0.04 | clean | 3.9 |
|  | ~120 mg UV 9390C |  |  |  |  |  |  |  |
| 27 | 6.5 g Drapex 6.8 | ~120 min | Out of Reactor | 0.8 | Avg | STD | FM |  |
|  | 6.5 g New Unidyme 14 | 140-148 C. | 3 Pass (50 ft/min) | 56 | 0.36 | 0.02 | clean |  |
|  | 0.5 g Adipic Acid |  |  |  |  |  |  |  |
|  | ~120 mg UV 9390C |  |  |  |  |  |  |  |
| 28 | 6.5 g Drapex 6.8 | 95 min | Out of Reactor | 0.5 | Avg | STD | FM |  |
|  | 6.5 g New Unidyme 14 | 140-143 C. | 3 Pass (50 ft/min) | 34 | 1.03 | 0.04 | cohesive |  |
|  | 0.5 g Adipic Acid |  | 5 Pass (50 ft/min) | 38 | No Testing Done |  |  |  |
|  |  |  | 7 Pass (50 ft/min) | 43 |  |  |  |  |
| 29 | 6.5 g Drapex 6.8 | 75 min | Out of Reactor | 0.6 | Avg | STD | FM |  |
|  | 6.5 g New Unidyme 14 | 140-148 C. | 3 Pass (50 ft/min) | 38 | 1.19 | 0.1 | stain | 26.7 |
|  | 0.5 g Adipic Add | 2 step | 5 Pass (50 ft/min) | 42 | 0.85 | 0.05 | clean | 10K |
|  | ~100 mg UV 9390C |  |  |  |  |  |  |  |
| 30 | 6.5 g Drapex | 130 min | Out of Reactor | 0.1 | Avg | STD | FM |  |
|  | 6.5 g New Unidyme 14 | 140-141 | 3 Pass (50 ft/min) | 49 | 0.56 | 0.04 | clean | 10K |
|  | 0.5 g Adipic | 2 Step | 5 Pass (50 ft/min) | 49 | 0.59 | 0.05 | clean |  |
|  | 0.196 g PC-205 |  |  |  |  |  |  |  |

TABLE 5-continued

| Example # | Components | Heat Cure Conditions | UV cure Dose | % Gel | Peel (SS) Avg | lbs/in STD | Failure Mode (FM) | Shear (min) |
|---|---|---|---|---|---|---|---|---|
| 31 | 6.5 g Drapex 6.8<br>6.5 g New Unidyme 14<br>0.5 g Adipic Acid<br>1.02 wt % PC-2506 | 105 min<br>140-144 C.<br>2 step | Out of Reactor<br>3 Pass (100 ft/min)<br>5 Pass (100 ft/min) | —<br>50<br>51 | Avg<br>0.59<br>0.64 | STD<br>0.02<br>0.02 | FM<br>Clean<br>Clean | 10K<br>(American UV) |
| 32 | 6.5 g Drapex 6.8<br>6.5 g New Unidyme 14<br>0.5 g Adipic Acid<br>1.00 wt % PC-2506 | 120 min<br>140-144 C.<br>2 step | Out of Reactor<br>1 Pass (100 ft/min)<br>3 Pass (100 ft/min)<br>3 Pass (150 ft/min) | 1<br>42<br>48<br>41 | Avg<br>0.9<br>0.48<br>0.84 | STD<br>0.07<br>0.1<br>0.05 | FM<br>clean<br>clean<br>clean | (American UV) |

Examples 33-45

Examples 33 to 45 were prepared to investigate potential scale up of the reactions according to the following procedure: 26 g DRAPEX 6.8, 26 g EMPOL 1062 and 2 g adipic acid were reacted at 140° C. for 220 min with mechanical mixing. The samples were then formulated by roll-mixing with PAGs at about 70° C. and the process was repeated until a homogeneous solution was obtained. The resulting formulations were then heated to 70° C. immediately before coating to about 2-4 mil gap. Curing was performed on a conveyer system equipped with medium pressure Hg lamp with at about 75 mJ/cm$^2$ dose at 150 ft/min of web speed. The compositions were processed successfully, indicating that these formulations may be scaled up properly. The resulting samples were analyzed for % gel, 180 degree peel off SS and shear (½×½×500 g). Table 6 summarizes the key performance data, The results indicate the following: (a) %-gel was consistent and high (for UV cured samples) and generally scaled well with UV energy, i.e. longer exposure (lower line speed) yielded slightly higher % gel, (b) adhesive performances were consistent with low standard deviations, and generally scaled with UV energy (flux and line speed), and (c) failure mode for all the samples off SS substrate was adhesive.

TABLE 6

| Example # | Type of PAG | Amount of PAG | Number of passes × speed (ft/min) | % Gel | Substrate | Avg. Peel (lbf/in) | Failure Mode | Shear min. |
|---|---|---|---|---|---|---|---|---|
| 33 | w no PAG and no UV cure | | | 2.2 | | | | |
| 34 | PC2506 | 0.75% | 3 × 100 | 45.9 | SS | 0.78 | clean | 10000+ min. |
| 35 | PC2506 | 0.75% | 3 × 125 | 45.6 | SS | 0.79 | clean | 5.1 min. |
| 36 | PC2506 | 0.75% | 3 × 150 | 43.6 | SS | 1.11 | clean | 5.7 min. |
| 37 | PC2506 | 1% | 3 × 100 | 46.7 | SS | 0.67 | clean | 7.8 min. |
| 38 | PC2506 | 1% | 3 × 125 | 44.7 | SS | 0.58 | clean | 10000+ min. |
| 39 | PC2506 | 1% | 3 × 150 | 43.7 | SS | 0.94 | clean | 0 min. |
| 40 | UVI6976 | 1.50% | 3 × 100 | 48.0 | SS | 0.90 | clean | 10000+ min. |
| 41 | UVI6976 | 1.50% | 3 × 125 | 47.3 | SS | 1.20 | clean | 10000+ min. |
| 42 | UVI6976 | 1.50% | 3 × 150 | 46.9 | SS | 0.95 | clean | 2237.5 min. |
| 43 | UVI6976 | 2% | 3 × 100 | 48.0 | SS | 0.88 | clean | 10000+ min. |
| 44 | UVI6976 | 2% | 3 × 125 | 48.8 | SS | 0.69 | clean | 10000+ min. |
| 45 | UVI6976 | 2% | 3 × 150 | 46.2 | SS | 1.09 | clean | 50.6 min. |

Example 46

DRAPEX 6.8/UNIDYME 14/adipic acid (6.5 g/6.5 g/0.5 g). The reaction was allowed to proceed with 2 g of DRAPEX 6.8 initially and the remaining 4.5 g were added over 0.5 to 1.5 hours.

Example 47

4.5 g of DRAPEX 6.8 was added initially and 2 g was added after initial viscosity increase (indicated by monitoring the rotation of the magnetic stir bar) and reaction was allowed to proceed to second viscosity buildup.

The viscosity of examples 46 and 47 was about 150 cP at 80° C., indicating to the ability to achieve high viscosity using fed-batch without significant gelation. When cured with 1.5 wt % UVI-6976, both samples showed peel force greater than 1.2 lbs/in.

For examples 48 through 54, the formulations were either prepared in a one step process, or a two step process as noted under the column 'Condition' for each of the examples in their respective table. In a one step process, the photo catalyst was added at the end of the initial polymerization without cooling the pressure sensitive adhesive precursor down to ambient condition. In a two step process, the pressure sensitive adhesive precursor was cooled down to ambient condition. The photo catalyst was added and mixed at about 80 to 100° C. The mixture was then coated and subjected to further curing reactions.

Examples 48-50

Examples 48 to 50 were prepared according to the procedure set forth in example 5 with varying amount of PC-2506. Each sample was exposed to various amount of radiation through passing under a medium pressure Hg lamp on a conveyer system at nominal dose of 75 mJ/cm$^2$ dose (measured at 150 ft/min) at various line speed and up to 3 times. All samples demonstrated acceptable peel and percent gel as shown in Table 7. Example 49 demonstrated good shear even at 150 ft/min.

TABLE 7

| Example # | Sample composition | Condition | UV cure condition | gel (%) | peel (lbs/in) | | | shear (min) |
|---|---|---|---|---|---|---|---|---|
| | | | | | Avg | STD | FM | |
| 48 | 6.5 g Drapex 6.8 | 120 min | Out of Reactor | 1 | Avg | STD | FM | |
| | 6.5 g New Unidyme 14 | 140-144 C. | 1 Pass (100 ft/min) | 42 | 0.9 | 0.07 | clean | 1.8 |
| | 0.5 g Adipic Acid | 2 step | 3 Pass (100 ft/min) | 48 | 0.48 | 0.1 | clean | — |
| | 1.00 wt % PC-2506 | | 3 Pass (150 ft/min) | 41 | 0.84 | 0.05 | clean | 840.0 |
| 49 | 6.5 g Drapex 6.8 | 100 min | Out of Reactor | 1 | Avg | STD | FM | |
| | 6.5 g New Unidyme 14 | 140-148 C. | 1 Pass (100 ft/min) | 32-37 | 0.92 | 0.09 | clean | 296.1 |
| | 0.5 g Adipic Acid | 2 step | 1 Pass (125 ft/min) | 23-32 | 0.95 | 0.03 | clean | 114.8 |
| | 1.00 wt % PC-2506 | | 1 Pass (150 ft/min) | 15-29 | 1.07 | 0.06 | clean | 2285.2 |
| 50 | 6.5 g Drapex 6.8 | 110 min | Out of Reactor | 0.3 | Avg | STD | FM | |
| | 6.5 g New Unidyme 14 | 140-143 | 3 Pass (100 ft/min) | 43 | 1.17 | 0.1 | clean | 10.8 |
| | 0.5 g Adipic Acid | 2 step | 3 Pass (125 ft/min) | 39 | 1.18 | 0.1 | clean | 2.7 |
| | 0.75% wt % PC-2506 | | 3 Pass (150 ft/min) | 34 | 1.39 | 0.1 | clean/mix | 285 |

Examples 51 and 52

Examples 51 and 52 were prepared as following: 6.5 g of DRAPEX 6.8 and 6.5 g of UNIDYME14 were reacted at 140° C. in the presence of 4 drops of dimethyl benzyl amine. The polymer was formulated with 3 wt % UVI-6976 in example 51 and 1.5 wt % of UVI-6976 in example 52. Table 8 is a summary of the processing conditions and the % gel of each sample. With about 3% UVI 6976 high gel values can be achieved regardless of UV dose. On the other hand, 1.5% UVI-6976 yielded low percent gel under similar processing conditions. The results suggest that a minimum PAG concentration is needed to neutralize the initial base. It was also observed the presence of UVI-6976 affected the thermal route as well, where the coating was still oily even after 160° C./60 min. When dimethyl benzyl amine was increased to 1%, the polymer started to cross-link at room temperature and was difficult to coat.

TABLE 8

| Example # | Components | Conditions | Dose lamp intensity/speed/ number of passes | % Gel |
|---|---|---|---|---|
| 51 | 6.5 g Drapex 6.8 | 90 min | no gel out of reactor | |
| | 6.5 g Unidyme 14 | 140-148 C. | 300WPI/150 fpm/1x | 62 |
| | 4 drops DmBA | 2 step | 300WPI/100 fpm/1x | 68 |
| | 0.92 (3%) UVI 6976 | | 200WPI/150 fpm/1x | 39 |
| | | | 200WPI/100 fpm/1x | 56 |
| | | | 125WPI/150 fpm/1x | 63 |
| | | | 125WPI/100 fpm/1x | 57 |
| 52 | 6.5 g Drapex 6.8 | 120 min | no gel out of reactor | |
| | 6.5 g Unidyme 14 | 140-145 C. | 300WPI/150fpm/1x | 3 |
| | 4 drops DmBA | 2 step | 300WPI/100fpm/1x | 7 |
| | 0.16 (1.5%) UVI 6976 | | 200WPI/150fpm/1x | 2 |
| | | | 200WPI/100fpm/1x | 2 |
| | | | 125WPI/150fpm/1x | 3 |
| | | | 1.25WPI/100fpm/1x | 1 |

Examples 53 and 54

In examples 53-54, several UV curable ESO/dimer diacid polymer compositions were prepared by adding 2, 4 and 5 wt % of Foral-85 (Arizona Chemicals). Summary conditions and results are provided in Table 9. The base polymer was heated to 140° C. followed by addition of Foral-85 at ca. 100° C. prior to addition of PAG. The samples showed consistent high percent gel and some promising peel and shear performance at low dose and high speed (American UV, 200 watts per inch (WPI), 150 fpm).

TABLE 9

| Example # | Components | Conditions | Dose lamp intensity_speed_number of passes | % Gel | Peel lbs/in Stainless Steel | | | Peel lbs/in HDPE | | | Shear (min) |
|---|---|---|---|---|---|---|---|---|---|---|---|
| | | | | | Avg | STD | FM | Avg | STD | FM | |
| 53 | 13.0 g Drapex 6.8 | 90 min | Out of Reactor_1 | 0.6 | Avg | STD | FM | Avg | STD | FM | |
| | 13.0 g Unidyme 14 | 140-146 C. | 300WPI_100fpm_1x | 49 | 0.9 | 0.08 | clean | 0.5 | 0.02 | clean | |
| | 1.0 g Adipic Acid | 2 step | 300WPI_150fpm_1x | 48 | 0.9 | 0.04 | clean | 0.4 | 0.03 | clean | 10000+ |
| | 2.5 wt % UVI 6976 | | 200WPI_100fpm_1x | 48 | 0.8 | 0 | 50% Tr | no sample left | | | 154 |
| | 4% Foral 85 | | 200WPI_150fpm_1x | 47 | 1 | 0.02 | clean | 0.5 | 0.03 | clean | 10000+ |
| | 2% Foral 85 | | Out of Reactor_2 | 0.6 | | | | | | | |
| | | | 300WPI_50fpm_1x | 53 | 0.5 | 0.01 | clean | 0.2 | 4E-04 | clean | 10000+ |
| | | | 300WPI_100fpm_1x | 49 | 0.6 | 0.1 | clean | 0.2 | 0.004 | clean | 3500 |
| | | | 300WPI_150fpm_1x | 49 | 0.7 | 0.01 | clean | 0.2 | 0.05 | clean | 10000+ |
| | | | 200WPI_100fpm_1x | 49 | 0.7 | 0.03 | clean | 0.2 | 0.05 | clean | 10000+ |
| | | | 200WPI_150fpm_1x | 41 | 0.9 | 0.1 | clean | no sample left | | | |

TABLE 9-continued

| Example # | Components | Conditions | Dose lamp intensity_speed_number of passes | % Gel | Peel lbs/in Stainless Steel | | FM | Peel lbs/in HDPE | FM | Shear (min) |
|---|---|---|---|---|---|---|---|---|---|---|
| | | | | | Avg | STD | | | | |
| 54 | 6.5 g Drapex 6.8 | 120 min | Out of Reactor | 1 | | | FM | | | |
| | 6.5 g Unidyme 14 | 140-142 C. | 300WPI_50fpm_1x | 38 | 0.9 | 0.03 | stain | | | |
| | 0.5 g Adipic Acid | cooled to 93 C. | 300WPI_100fpm_1x | 30 | 0.5 | 0.2 | cohesive | | | |
| | 2.0 wt % UVI 6976 | 1 step | 300WPI_150fpm_1x | 30 | 0.3 | 0.1 | cohesive | | | |
| | 5% Foral 85 | | 300WPI_100fpm_2x | — | 0.7 | 0.05 | stain | | | |

Example 55

A DRAPEX 6.8/UNIDYME 14/adipic acid base polymer was formulated at 0.25 wt % and 0.66 wt % of UVI-6976 respectively. The samples were screened using visual observations and thumb tack. Samples were cured at 50 fpm, 75 fpm and 100 fpm (all at 300 WPI, American UV). Within 1 hr after the UV dose was provided, all samples at 0.66 wt % of UVI-6976 appeared fully cured. At 0.25 wt % of UVI-6976; a thermal step (70° C./60 s) was used to fully cure the 50 fpm and 75 fpm samples.

Example 56

A DRAPEX 68/UNIDYME 14/adipic acid base polymer was formulated with 1 wt % of UVI-6976 and 1 wt % of tetra (ethylene glycol dimethyl ether) or pentaerythritol. Both the samples were tacky and slightly over cured even at a dosage of 200 WPI and 150 fpm.

Example 57

Compatibility of PAGs with acids and alcohols. Compatibility of acids with PAGs was tested by curing a DRAPEX 6.8 sample in presence of such acids. Under similar conditions, when DRAPEX 6.8 will rapidly form a film, in the presence of PRIPOL 1013, after 90 s of UV exposure, no discernible viscosity build up was observed. As a control experiment, it was observed that DRAPEX 6.8 will polymerize/crosslink to a solid film in presence of 1% UVI-6976 and 50% acrylic acid (by wt. of epoxidized vegetal oil) at even 10 s of UV (90 mW/cm$^2$) exposure. Acrylic acid by itself did not respond to cationic polymerization.

Example 58

Epoxidized vegetable oil was mixed with PAGs at about 99:1 weight ratio. The mixture was exposed to Intelliray 400 desktop UV systems from Uvitron Inc. equipped with a WPI metal halide lamp with a flux of about 90 mW/cm$^2$ (UV-A) for a period of 5 seconds to 90 seconds. The sample was further heat cured with a 250 WPI infrared lamp about 10 inches under the lamp. Table 10 is a summary of the observations.

TABLE 10

| ESO | PAG | Observations |
|---|---|---|
| Drapex 6.8 | UVI-6992 | uncured |
| Drapex 6.8 | UVI-6976 | cured |
| Drapex 6.8 | UV 9390C | cured |
| Drapex 6.8 | PC-2506 | cured |
| Edenol D81 | UVI-6992 | uncured |
| Edenol D81 | UVI-6976 | cured |
| Edenol D81 | UV 9390C | cured |
| Edenol D81 | PC-2506 | cured |
| Vikoflex 5025 | | |
| Vikoflex 5075 | UVI-6976 | uncured |
| Vikoflex 5075 | UV 9390C | uncured |

Example 59

In order to assess the effect of blending on Tg and cure rate—ESO were blended with hydroxyl terminated polybutadiene in ratios of 50:50 and 75:25, followed by addition of UVI-6976 (1% by wt. of ESO) and application of various cure conditions. The results are summarized in Table 11. A lower amount of ESO leads to lower degree of cure,

TABLE 11

| | | Cure Conditions, seconds | | |
|---|---|---|---|---|
| | ESO:OH-Polybutadiene ratio | UV @ 90 mW/cm2 | IR lamp | Observations |
| Drapex 6.8 | 50:50:00 | 30 | 60 s | Slightly cured |
| | | 90 | | Tacky/brittle |
| | 75:25:00 | 5 | | Almost cured |
| | | 20 | | Fully cured |
| | | 30 | | Fully cured |
| Edenol D81 | 50:50:00 | 60 | | Not fully cured |
| | | 90 | | Tacky, not fully cured |
| | 75:25:00 | 30 | | Slightly cured |
| | | 60 | | Fully cured |

Example 60

Figure 3:
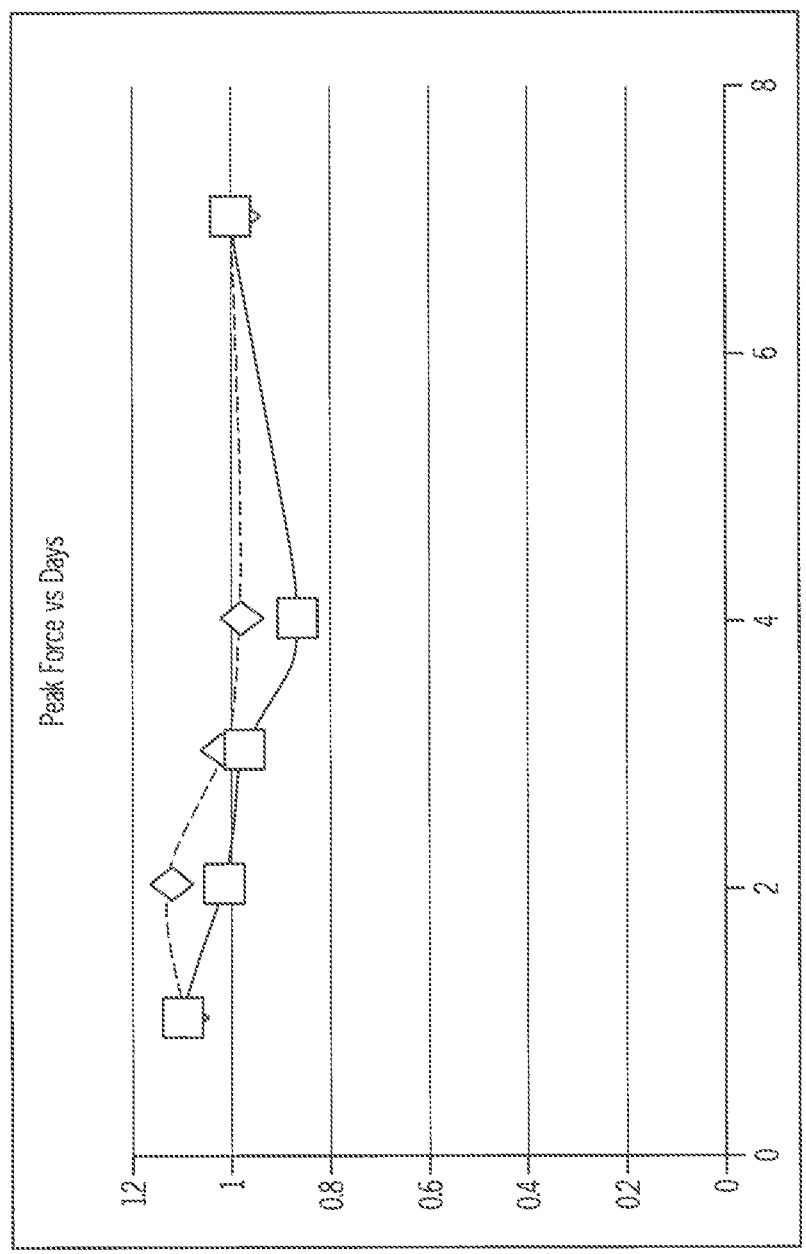
FIG. 3 is a SPAT plot showing the peak force versus time on one example according to one embodiment of the invention.

DRAPEX 6.8 and UNIDYME 14 in an amount of 6.5 g each were mixed in a 50 mL round bottom flask using a magnetic stir bar and heated to 140° C. in a heating mantle. The mixture was polymerized for 20 minutes, then 10 drops of photoinitiator (UVI-6976) was added. The mixture was mixed for about 15 minutes. The polymer was coated on a 1 mil PET film. Two samples prepared accordingly were cured under Intelliray –400 UV lamps with about 90 mW/cm$^2$, for 20 seconds and 30 seconds respectively. The percent gel for the sample cured for 20 seconds was 54%, and that for the sample cured for 30 seconds was 62%. The stability of the sample over time was studied using SPAT. FIG. 3 shows the change in peak force in Newton over time respectively in a total of 7 days. The data shows that the samples are relatively stable over time.

Example 61

The sample was prepared as according to the procedure set forth in example 60, except that less than 10 wt % of mono and difunctional epoxy DER 732, 1, 2-Epoxydodecane and Epon Resin 862 were each added at the time of PAG (UV-6976) addition for three individual samples. Each of the sample demonstrated ~0.5 lb/in peel (ss), shear (>10 K min, ½×½×500 g) and stable SPAT measurements over one week of data collection. The results demonstrated that the small amount mono and difunctional epoxy can further help in modulating the adhesion stability.

Example 62

DEHYSOL D81 and UNIDYME 14 in an amount of 6.5 g each were mixed in a 50 mL round bottom flask using a magnetic stir bar and heated to 145° C. in a heating mantle. The mixture was polymerized for 150 minutes, then 20 drops of photoinitiator (UVI-6976) was added. The mixture was mixed for about 15 minutes. The polymer was coated on a 1 mil PET film. Three samples prepared accordingly were cured under Lesko Conveyer UV system fitted with a magnetron driven Uvitron D-bulb with a dose of 225 ml/cm$^2$ (1.3 W/cm$^2$) at 50 ft/min in the center of conveyer, at 50 ft/min for 3 passes, 5 passes, and 7 passes respectively. The percent gel for the sample fresh out of the flask was 0.2%, and that became 52%, 53% and 54% for the samples that passed through the UV curing at 3 passes, 5 passes and 7 passes respectively The average peel force on stainless steel was 0.88 lbs/in, 0.81 lbs/in and 0.9 lbs/in for the three samples respectively. The shear for all three samples was over 10,000 mins.

Example 63

A batch reaction of DRAPEX 6.8 (D)/EMPOL 1062 (E)/adipic acid (A) was formulated with PC 2506 and UVI-6976 separately and coated to a 2 mil gap, followed by UV plus thermal curing (70° C./5 min). Compositions were cured on American Ultraviolet (medium pressure mercury) not only at different web speeds (100 fpm, 150 fpm) and at different lamp intensities (300 watts per inch (WPI), 200 WPI, 125 WPI). The two step curing was implemented as follows: first, providing a proper UV dose followed by thermal cure either at 70° C./5 min or at 50° C./5 min. Table 12 summarizes the results.

TABLE 12

| Sample | Photo catalyst (concentration) | # of passes × Line speed (ft/min) | Reaction Notes | % Gel | aged % Gel | Substrate | Avg. peel (lbs/in) | St. Dev (peel) | Failure mode |
|---|---|---|---|---|---|---|---|---|---|
| E63-initial | | | 13/13/1 for D/E/Adipic | 2.4 | 2.6 | | | | |
| E63-0.5-1 × 150 | PC 2506 (0.5%) | 1 × 150 | batch rxn run @ 140 C | | 56.4 | SS | 0.18 | 0.01 | cohesive |
| E63-0.5-3 × 150 | PC 2506 (0.5%) | 3 × 150 | formulated 0.5% 2506 | | 59.1 | SS | 0.50 | 0.01 | clean |
| E63-1%-1 × 150 | UVI-6976 (1%) | 1 × 150 | other half 1% UVI-6976 | | 53.5 | SS | 0.29 | 0.02 | cohesive |
| E63-1%-3 × 150 | UVI-6976 (1%) | 3 × 150 | | | 58.9 | SS | 0.59 | 0.03 | clean |

Example 64

A 30/70 fed batch was run at 140° C. followed by formulating either with 0.5 wt % of PC 2506 or 1 wt % of UVI-6976. The formulations were prepared and coated at about 70° C. to about 2-4 mil gap. The coating was UV cured at different line speeds (300 WPI) followed by a thermal post cure of 70° C./5 min. Table 13 summarizes the results.

TABLE 13

| Sample | Photo catalyst (concentration) | # of passes × Line speed (ft/min) | Reaction Notes | % Gel | Substrate | Avg. Peel (lbs/in) | St. Dev (Peel) | Failure Mode | Coat Wt. gsm |
|---|---|---|---|---|---|---|---|---|---|
| E64-initial | | | 13/13/1 for D/E/Adipic | 2.0 | | | | | 60-100 gsm. |
| E64-0.5-1 × 150 | PC 2506 (0.5%) | 1 × 150 | fed-batch 30/70 @30 min. | 51.1 | SS | 0.40 | 0.05 | clean | |
| E64-0.5-2 × 150 | PC 2506 (0.5%) | 2 × 150 | run @140 C. in 2-neck flask | 52.7 | SS | 0.60 | 0.2 | clean | |
| E64-0.5-3 × 150 | PC 2506 (0.5%) | 3 × 150 | 0.5 PC-2506, 1% UVI-6976 | 54.0 | SS | 0.42 | 0.2 | clean | |
| E64-1%-1 × 150 | UVI-6976 (1%) | 1 × 150 | | 34.9 | SS | 0.51 | 0.2 | cohesive | |
| E64-1%-3 × 150 | UVI-6976 (1%) | 3 × 150 | | 49.1 | SS | 1.18 | 0.3 | clean | |

Example 65

A fed batch (30/70) was run at 140° C. followed by formulation with 0.5 wt % of PC-2506 at about 70° C. The formulated mixture was coated to about 2-4 mil gap followed by exposure to UV at different line speeds (150 fpm and 100 fpm) and lamp intensity (300 WPI, 200 WPI and 125 WPI). The UV cured sample was further exposed to thermal cure step at 50° C. for 5 min. Table 14 summarizes the key results.

TABLE 14

| Sample | Lamp Intensity (WPI) | # of passes x Line speed (ft/min) | Reaction Notes | % Gel | Substrate | Avg. Peel (lbs/in) | St. Dev (Peel) | Failure Mode | Coat Wt. gsm |
|---|---|---|---|---|---|---|---|---|---|
| E65-initial | | | 6.5/6.5/0.5 for D/E/A fed-batch 30/70 @30 min. run @140 C. 0.5% PC 2506 | 1.6 | | | | | 30-40 gsm. |
| E65-125W-1 × 100 | 125 | 1 × 100 | | 56.3 | SS | 0.12 | 0.02 | clean | |
| E65-125W-1 × 150 | 125 | 1 × 150 | | 52.8 | 55 | 0.09 | 0.005 | clean | |
| E65-200W-1 × 100 | 200 | 1 × 100 | | 55.0 | SS | 0.13 | 0.01 | clean | |
| E65-200W-1 × 150 | 200 | 1 × 150 | | 54.9 | SS | 0.12 | 0.01 | clean | |
| E65-300W-1 × 100 | 300 | 1 × 100 | | 55.9 | SS | 0.12 | 0.01 | clean | |
| E65-300W-1 × 150 | 300 | 1 × 150 | | 54.8 | SS | 0.11 | 0.01 | clean | |

Example 66

A pilot batch of ESO/dimer acid adhesive was prepared utilizing a five gallon wiped walled reactor. The recipe for the pilot batch is shown in Table 15:

TABLE 15 batch scale 16.81 Lbs

| Reactor Charge | % of batch | lbs |
|---|---|---|
| Unidyne 14 | 48.0% | 8.07 |
| Adipic Acid | 4.0% | 0.67 |
| Drapex 6.8 | 14.4% | 2.42 |
| reactor charge total | | 11.16 |
| Feed | | |
| Drapex 6.8 | 33.6% | 5.65 |
| feed total | 100.0% | 5.65 |
| total | | 16.81 |
| less samples | | 5.6 |
| net | | 11.21 |

| Post-Add | % BOR | lbs | g |
|---|---|---|---|
| CPI 6976 | 0.75% | 0.084 | 38.2 |
| post-add total | | 0.084 | 38.2 |

Figure 4:
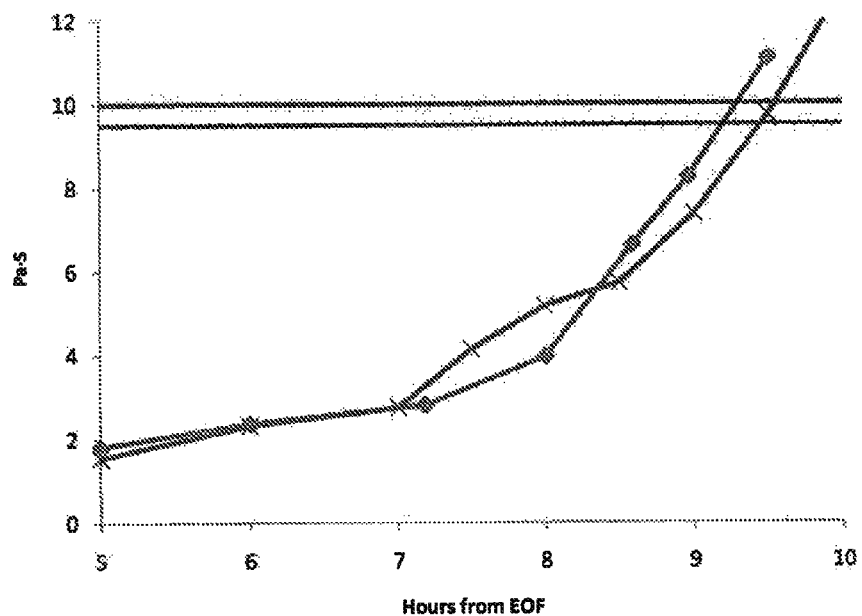
FIG. 4 is a chart showing the relationship between viscosity and time from EOF according to one embodiment of the invention.

Procedure:

Add reactor charge and set agitator to 40
Oil Bath set point to 130 C, start heating
Once batch at 120 C, hold for 30 minutes TABLE 15-continued (t = 30) At end of hold, start Drapex feed: 1 quart each 5 minutes withdraw viscosity sample every 60 minutes, then 30 minutes in late stage
Rxn is complete when 80 C viscosity is 9.5-10 Pa * sec
Take off 4 samples in 1 quart jars (each about 3/4 full/1.4 lbs)
Charge CPI 6976 post add
Apply vacuum
Hold until degassed or 10 minutes, whichever comes first TABLE 15-continued Release vacuum
Discharge into jacketed feed vessel for trial Viscosity for the batch was followed to determine the proper "B stage" of the material to stop the reaction and post add the photo initiator (CPI 6976), the target was 9.5-10 Pa*s, with the actual reaching 11 Pa*s, as shown in FIG. 4.

| Run sheet: | | | |
|---|---|---|---|
| time | Hours | Pa * sec | comment |
| 2:30 | | | reactor charge at 120 C. |
| 5:05 | 0.0 | | end of feed |
| 10:05 | 5.0 | 1.818 | sample 1 |
| 11:05 | 6.0 | 2.37 | |
| 12:16 | 7.2 | 2.801 | |
| 13:05 | 8 | 3.96 | |
| 13:40 | 8.58 | 6.625 | |
| 14:03 | 8.97 | 8.257 | |
| 14:35 | 9.5 | 11.08 | cooling |

Pilot Coating

The ESO/Dimer acid formulation was then heated to 80° C. in a water jacketed feed vessel under mechanical stirring.

Figure 5:
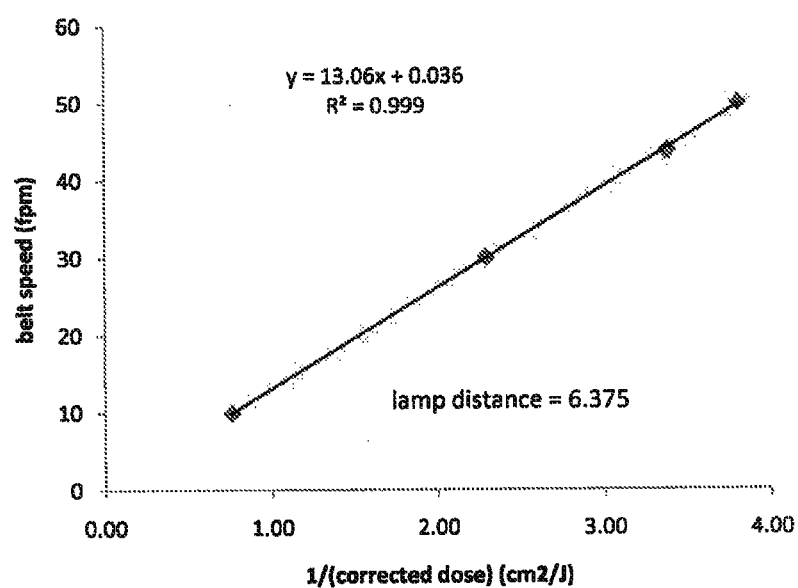
FIG. 5 is a chart showing the relationship between belt speed and correct dose$^{-1}$ for one lamp distance in one embodiment of the invention.

The coater was set up to coat on 2 mil PET liner, nipped to 50 lb semi gloss paper face stock. The coaters UV light was calibrated to get 300 ml/cm$^2$ at max line speed of 50 feet/min. After calibration it was determined that we would need to run at a line speed of 43.8 fpm to hit 300 mJ/cm$^2$ as shown in FIG. 5.

| belt speed | lamp dist | microcure | J/cm2 | cm2/J |
|---|---|---|---|---|
| 10 | 3 | 1.02 | 2.43 | 0.41 |
| 30 | 3 | 0.33 | 0.78 | 1.28 |
| 50 | 3 | 0.20 | 0.47 | 2.11 |
| 50 | 4 | 0.18 | 0.44 | 2.29 |
| 10 | 6.38 | 0.56 | 1.32 | 0.76 |
| 30 | 6.38 | 0.18 | 0.44 | 2.25 |
| 50 | 6.38 | 0.11 | 0.26 | 3.80 |
| 43.8 | 6.38 | 0.13 | 0.30 | 3.38 |

Coating was conducted at 43.8 fpm and the pump was adjusted to shoot for 20 gsm, actual coat weight was 17 gsm. The die had a 0.015" shim and was heated along with the delivery system to 80° C. Coating was conducted onto PET liner, passed through the (cold) oven and lamp, then nipped to the 50 lb paper.

The resultant material was allowed to equilibrate in a TAPPI room for 2 days prior to testing. The resultant material gave acceptable peel adhesion to HDPE, 0.95, 0.95, 0.93, 0.93 pli, all clean peels with no transfer.

All patents, published applications, and articles noted herein are hereby incorporated by reference in their entirety.

It will be understood that any one or more feature or component of one embodiment described herein may be combined with one or more other features or components of another embodiment. Thus, the present invention includes any and all combinations of components or features of the embodiments described herein.

It will be appreciated that various changes in the details, materials, and arrangements of components or operations, which have been herein described and illustrated in order to explain the nature of the invention, may be made by those skilled in the art without departing from the principle and scope of the invention, as expressed in the appended claims.

What is claimed is:

1. A method comprising:
   reacting an epoxidized naturally occurring oil or fat with at least one dimer acid to form a pressure sensitive adhesive precursor at an elevated temperature for a given period of time;
   mixing a photoacid generator with the PSA precursor to form an intermediate product;
   applying the intermediate product onto a carrier;
   UV radiation curing the intermediate product to form a PSA; and
   thermally post curing the PSA at a post curing temperature for a period of less than about 2 minutes.

2. The method of claim 1 wherein the naturally occurring oil or fat is selected from the group consisting of soybean oil, palm oil, olive oil, corn oil, canola oil, linseed oil, rapeseed oil, castor oil, coconut oil, cottonseed oil, palm kernel oil, rice bran oil, safflower oil, sesame oil, sunflower oil, tall oil, lard, tallow, fish oil and fats and oils from algae.

3. The method of claim 1, wherein the reacting step is conducted in a batch or a fed-batch fashion.

4. The method of claim 1, wherein the post curing is conducted using hot rollers.

5. The method of claim 1, further comprising adding at least one component selected from the group consisting of monoepoxides, monoacids, polyols, biobased polyols, UV enhancers, and catalysts to form the pressure sensitive adhesive precursor.

6. The method of claim 5, wherein the at least one additional component is a biobased polyol derived from castor oil.

7. The method of claim 1, further comprising adding at least one enhancer selected from the group consisting of crosslinkers, catalyst, co-initiators tackifiers, UV absorber, UV enhancer, and UV sensitizers to form the pressure sensitive adhesive precursor.

8. The method of claim 7, wherein the at least one enhancer is selected from the group consisting of methyltriethoxysilane, tetraethyl orthosilicate, 1,4-cyclohexanedimethanol diglycidyl ether, pentaerythritol, tetra (ethylene glycol dimethyl ether), bis(2,4,6-trimethylbenzoyl)-phenylphosphineoxide(IRGACURE 819), acetophenone, benzophenone, anthracene, and isopropyl-9H-thioxanthen-9-one (ITX).

9. The method of claim 1, further comprising adding a multifunctional molecule comprising at least one of hydroxyl, carboxylate, thiol, vinyl ether, silane, siloxane or epoxy functionalities to form the pressure sensitive adhesive precursor.

10. The method of claim 9, wherein the multifunctional molecule is selected from the group consisting of methyltriethoxysilane, tetraethyl orthosilicate, 1,4-cyclohexanedimethanol diglycidyl ether, pentaerythritol, and tetra(ethylene glycol dimethyl ether) and its derivatives.

11. The method of claim 1, wherein the UV radiation curing is performed in the presence of a cationic photoinitiator.

12. The method of claim 1, wherein the PSA has gel content of from 20% to 84%.

* * * * *